Figure 1C:
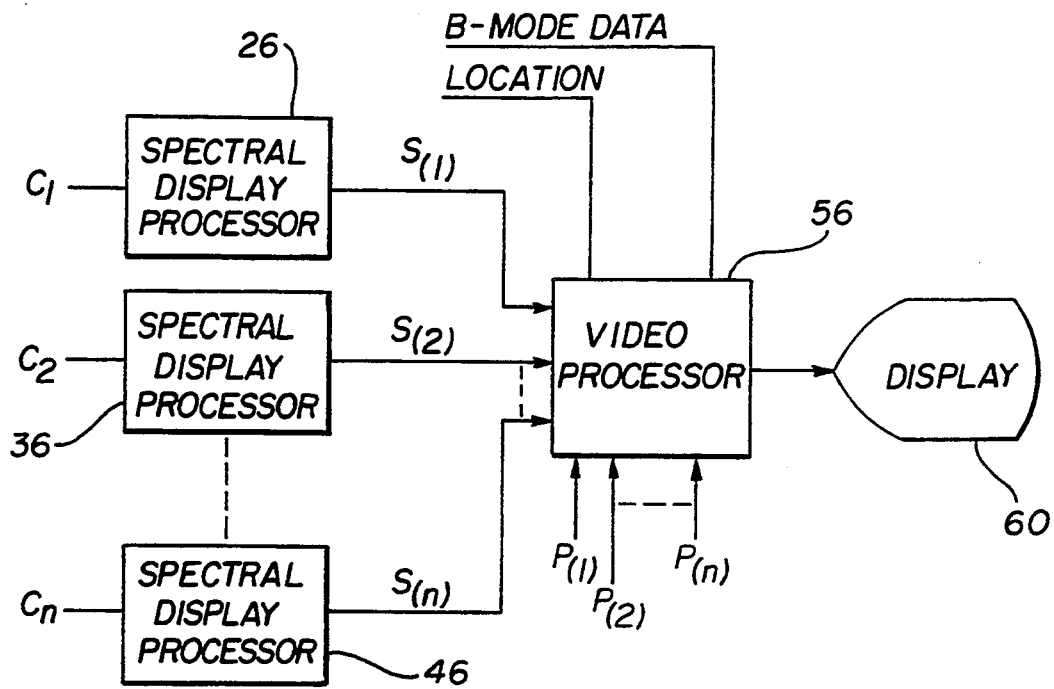

United States Patent [19]
Peterson

[11] Patent Number: 5,365,929
[45] Date of Patent: Nov. 22, 1994

[54] MULTIPLE SAMPLE VOLUME SPECTRAL DOPPLER

[75] Inventor: Roy B. Peterson, Redmond, Wash.

[73] Assignee: Advanced Technology Laboratories, Inc., Bothell, Wash.

[21] Appl. No.: 131,235

[22] Filed: Oct. 4, 1993

[51] Int. Cl.$^5$ .............................................. A61B 8/00
[52] U.S. Cl. .......................... 128/661.10; 128/661.09; 128/916
[58] Field of Search ...................... 128/660.05, 660.07, 128/661.09, 661.10, 916

[56] References Cited

U.S. PATENT DOCUMENTS

| | | | |
|---|---|---|---|
| 4,848,354 | 7/1989 | Angelsen et al. | 128/660.05 |
| 5,081,993 | 1/1992 | Kitney et al. | 128/916 |
| 5,197,477 | 3/1993 | Peterson et al. | 128/660.05 |
| 5,280,787 | 1/1994 | Wilson et al. | 128/661.10 |
| 5,282,471 | 2/1994 | Sato | 128/664.05 |

*Primary Examiner*—George Manuel
*Attorney, Agent, or Firm*—W. Brinton Yorks, Jr.

[57] ABSTRACT

An ultrasonic diagnostic system simultaneously monitors the Doppler signal of a plurality of sample volumes within the body of a patient which are aligned around a point of diagnostic interest within the body. The Doppler signal of the sample volume which best satisfies a predetermined criterion, such as that exhibiting the greatest Doppler signal power, is displayed to the user. When a different sample volume meets the criterion the Doppler signal display changes to display the Doppler signal of the newly identified sample volume. In one embodiment the spectral Doppler displays of a number of sample volumes are displayed concurrently and that which best satisfies the chosen criterion is identified to the user. In another embodiment the identified sample volume is identified in a B mode display of the sample volume area while the spectral Doppler display from the identified sample volume is displayed. The two dimensional B mode display can also be extended to a three dimensional display of a volume of individual sample volumes.

20 Claims, 7 Drawing Sheets

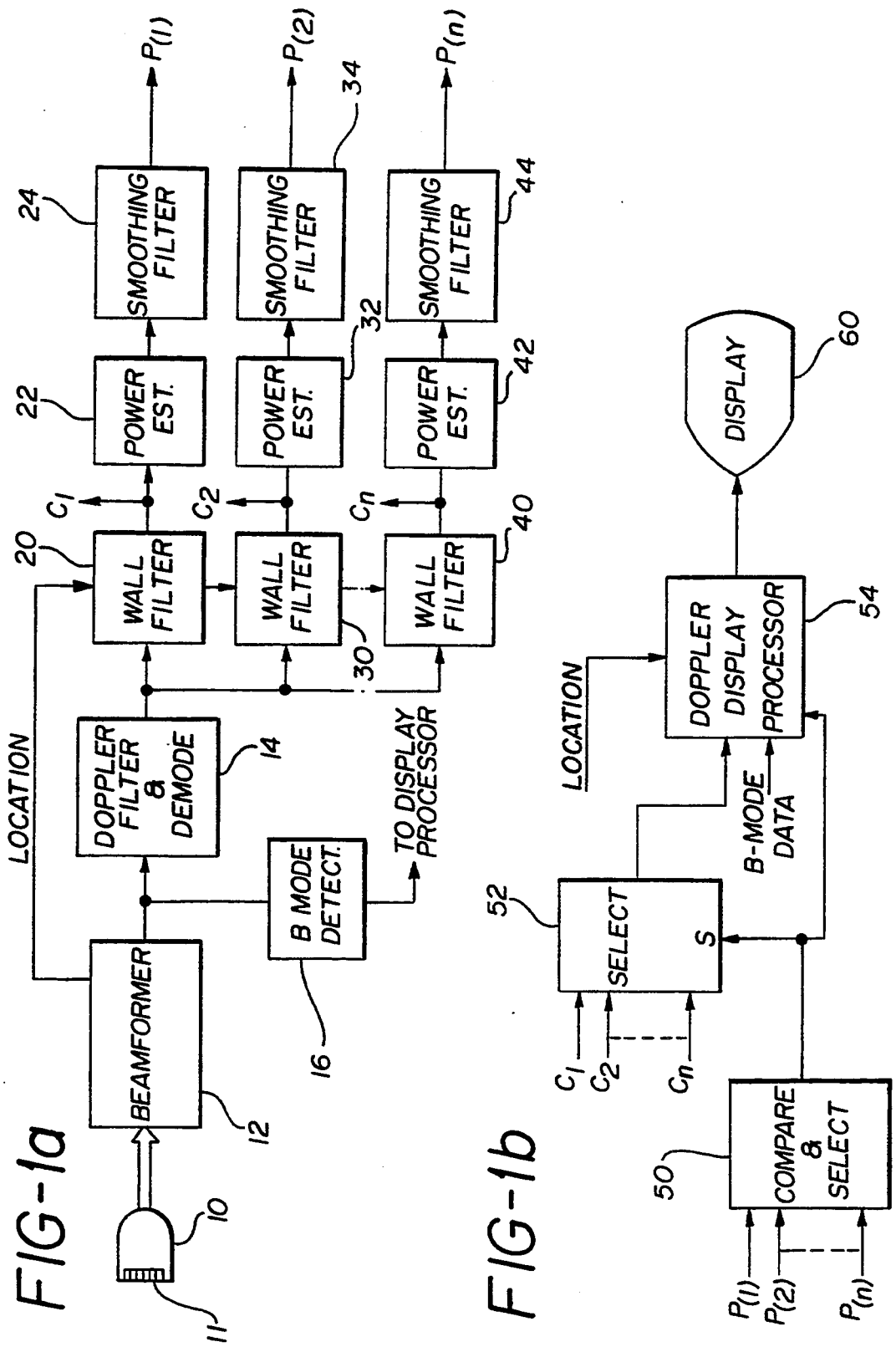

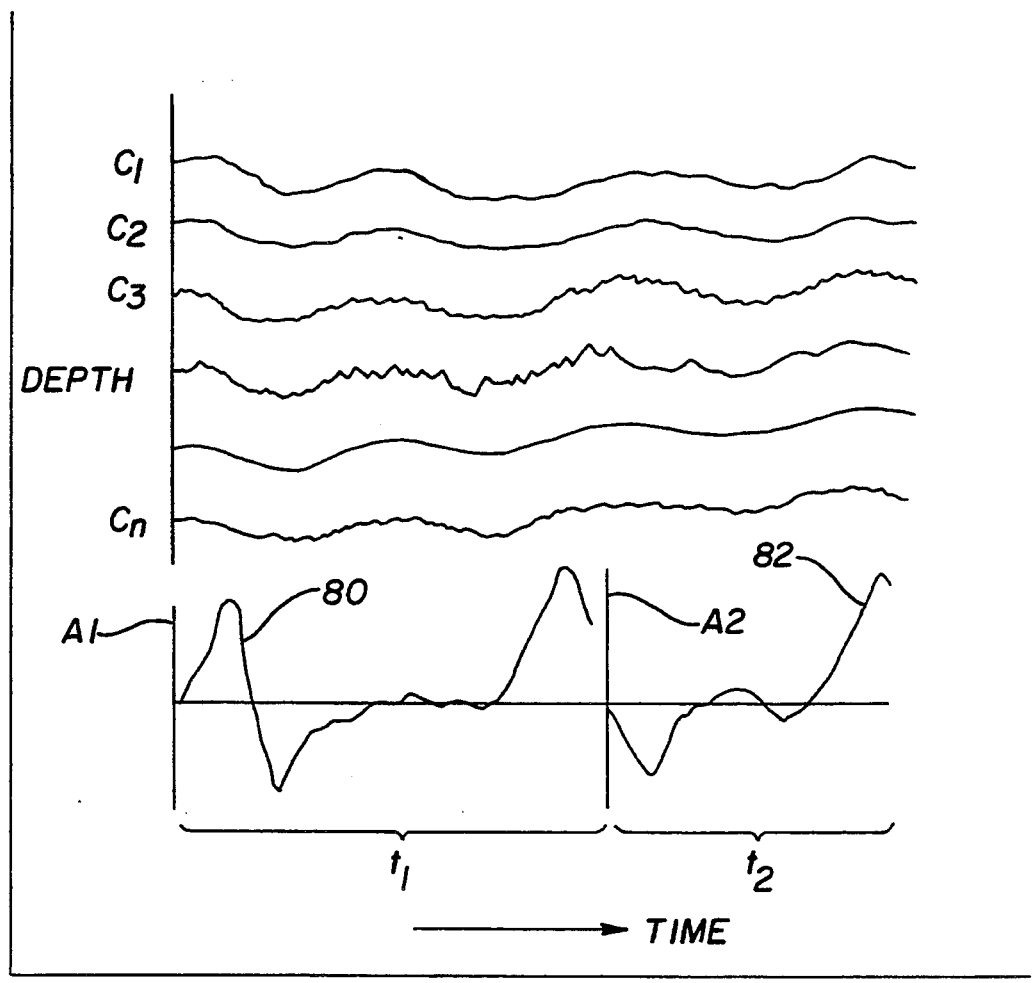

MULTIPLE SAMPLE VOLUME SPECTRAL DOPPLER

This invention relates to the use of ultrasonic diagnostic imaging systems for the measurement and diagnosis of flow conditions within the body and, in particular, to the use of ultrasonically derived spectral Doppler information for the measurement of the flow of blood and other fluids within the body.

Ultrasonic diagnostic systems are used to measure the flow of bodily fluids such as blood through the use of the Doppler principle. Typically, a sinusoidally modulated pulse train of ultrasonic energy is transmitted into the body toward the vessel or location where the measurement is to be made. The echo signals returned from the measurement location are compared in frequency or phase from pulse to pulse and the difference, or Doppler shift, is displayed in some form. The Doppler shift is proportional to the speed of the flowing fluid with the sense of the shift indicating direction in relation to the ultrasonic scanhead. One conventional way to display such Doppler information is as a time frequency representation of the received Doppler signal. This time frequency representation, known as spectral Doppler, is usually displayed graphically in real time, with the frequency content of the display indicating the speed of fluid flow.

The traditional method for acquiring spectral Doppler information is to move the transducer over the skin of the patient to scan the beam while listening for the characteristic Doppler sounds of pulsating fluids. The spectral Doppler measurements are then examined while the Doppler sounds are being steadily received. An improved technique for acquiring spectral Doppler information is to acquire a two dimensional B mode image of the vessel or organ where fluid flow is to be measured. A visual pointer over the image indicates the path of the Doppler beam and a cursor intersects the pointer at the depth or range at which the Doppler measurement is to be taken. The intersection of the two is maintained at the point in the image of the vessel or organ where flow is to be measured while the user views the spectral Doppler data.

However, difficulties are often encountered with either the audible or visual technique. The point in the body from which Doppler signals are to be acquired is called the sample volume, and is defined by the distance from the transducer to the cursor and pointer intersection. Generally the physician wants to make the sample volume as small as possible so as to interrogate only the precise spatial volume of interest. But to allow for human error in the placement of the sample volume it is desirable to make the sample volume relatively large. In addition, it is often difficult to hold the sample volume at precisely the same point in the body. As the transducer and body move relative to each other, so does the intersection point relative to the intended sample volume point in the body. The hand of the physician can inadvertently move the transducer during the examination, the patient can move, and reflexive movement such as breathing can cause the sample volume location to vary. Maintaining the sample volume in continual alignment with a very small vessel or point in the body is difficult even under the best of conditions.

In accordance with the principles of the present invention the accuracy and precision of spectral Doppler measurement are enhanced by utilizing a plurality of spatially related sample volumes, the signal returns from which are monitored by the ultrasound system. The spectral Doppler information which is used or displayed is that which is derived from the sample volume having the greatest signal return, where signal return may be measured in amplitude, frequency, power, or some other signal characteristic. The spatially related sample volumes may be arranged as a two or three dimensional grid of sample volumes or as a sequence of sample volumes linearly arranged along the pointer for the Doppler path. In a preferred embodiment the several sample volumes are displayed in relation to a B mode image, and the sample volume from which the spectral Doppler information is derived is indicated to the user.

Figure 2:
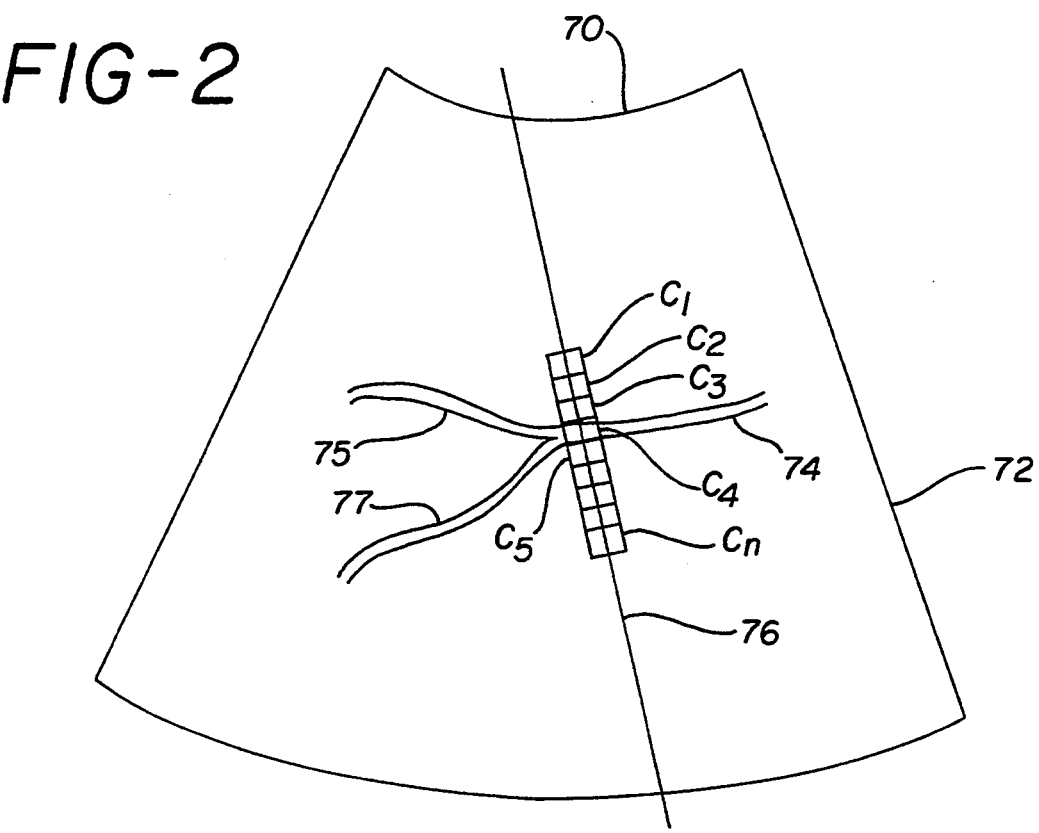
Figure 3:
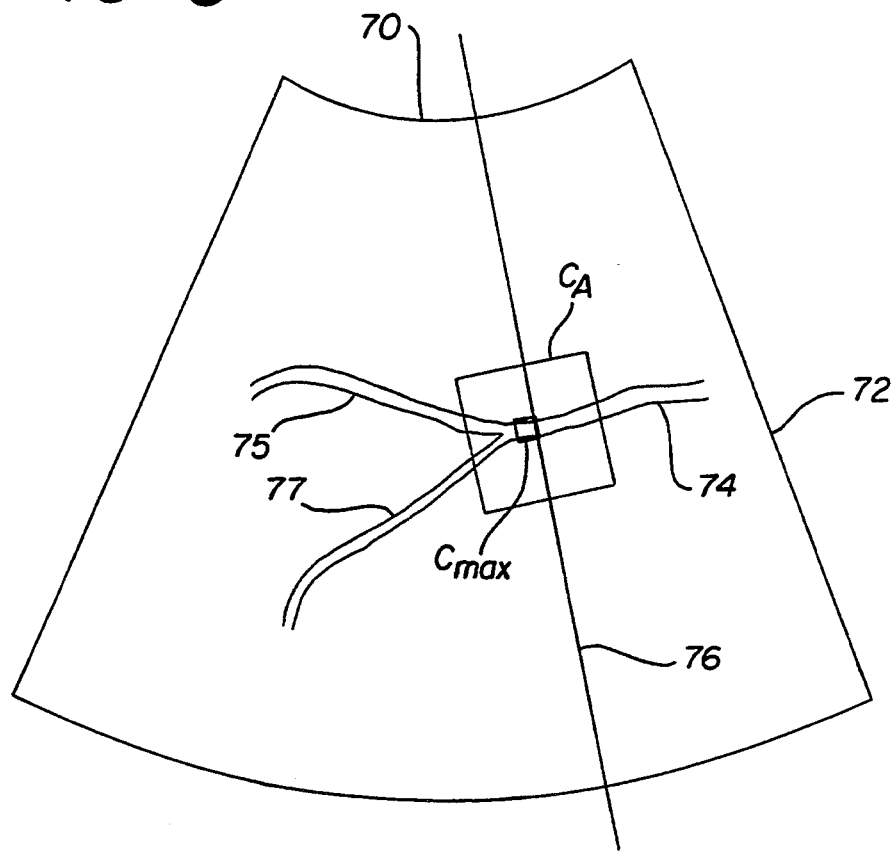
Figure 6:
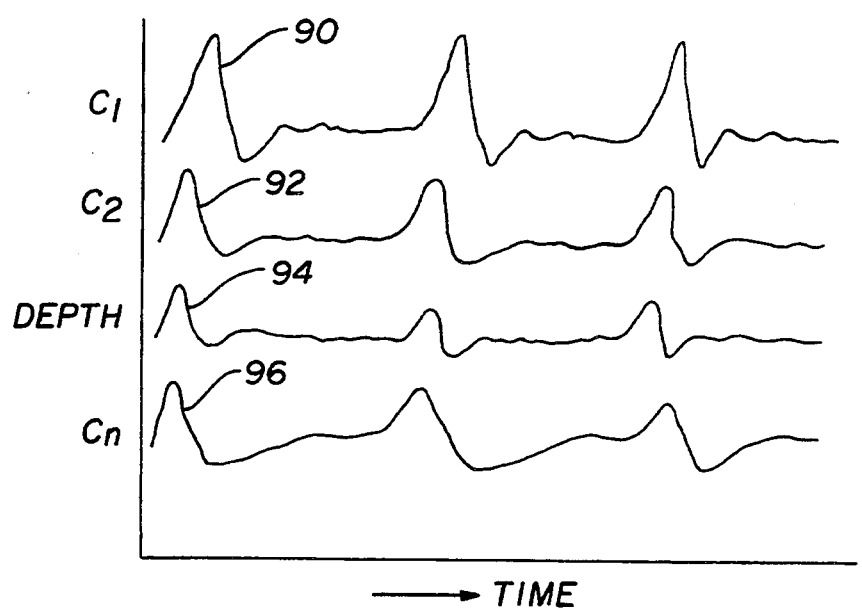
Figure 4:
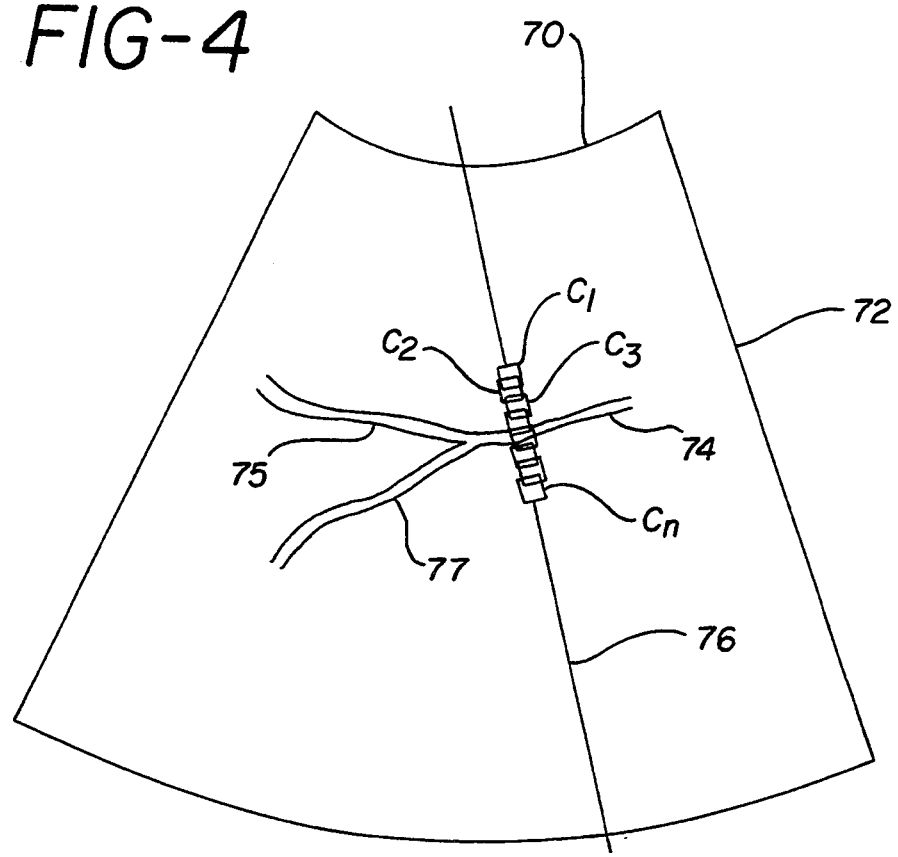
Figure 9:
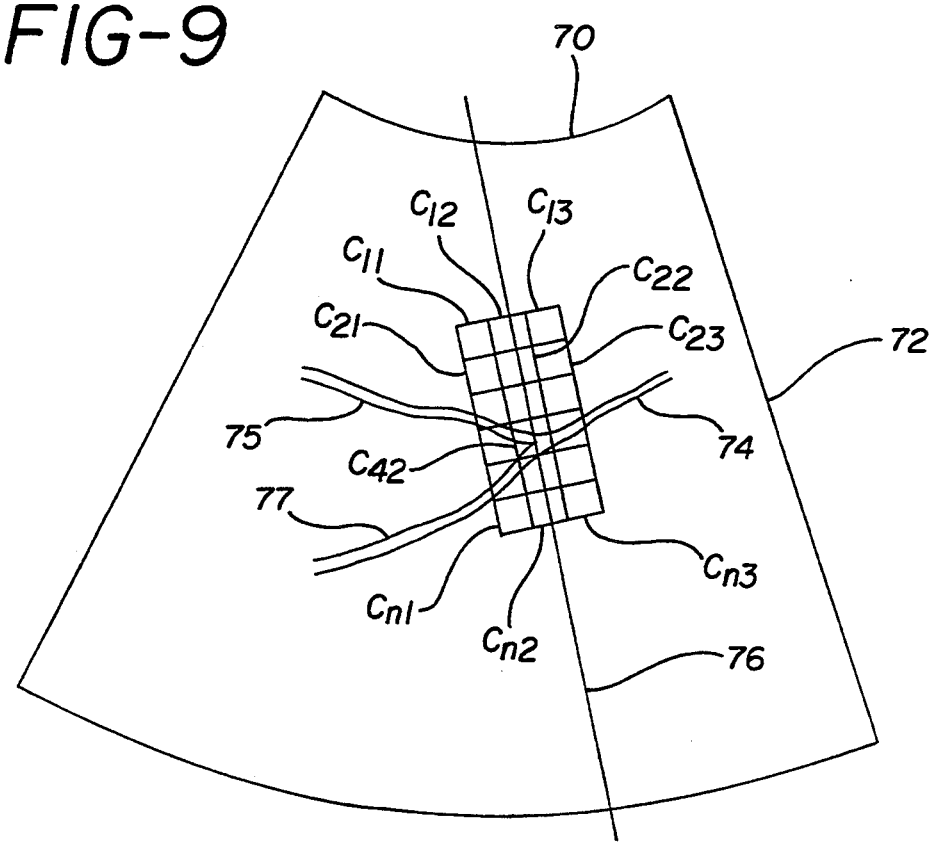
Figure 7:
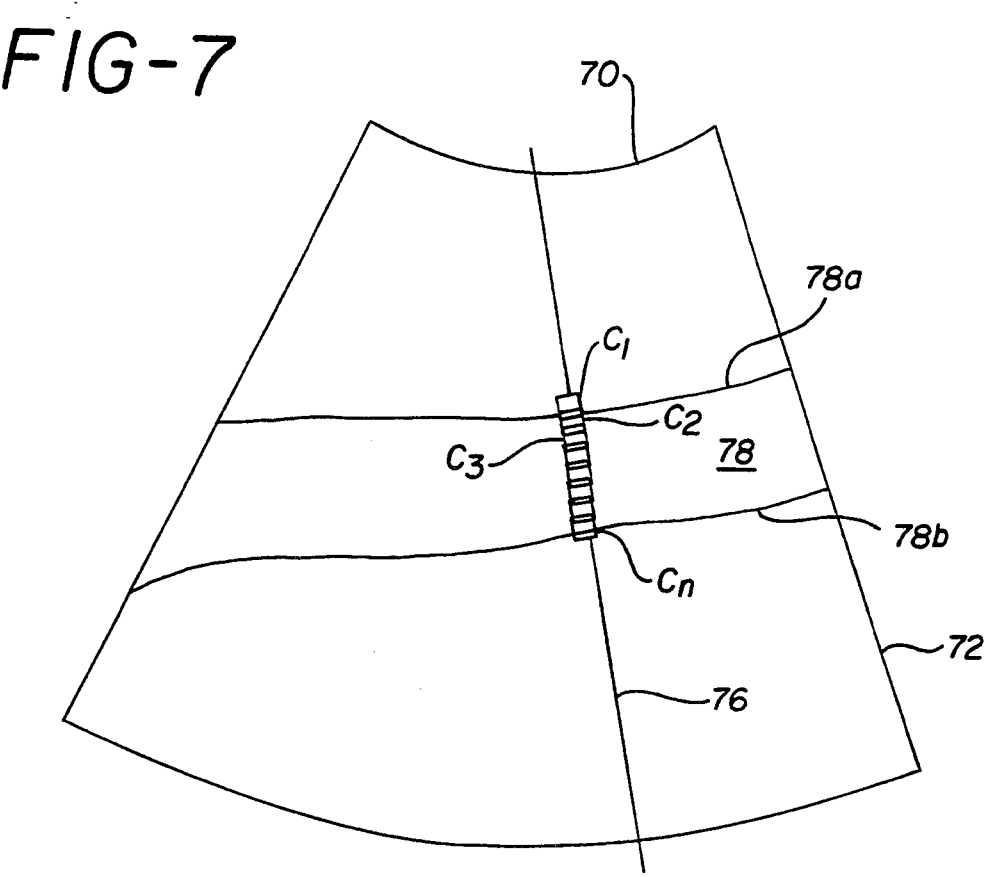
Figure 11:
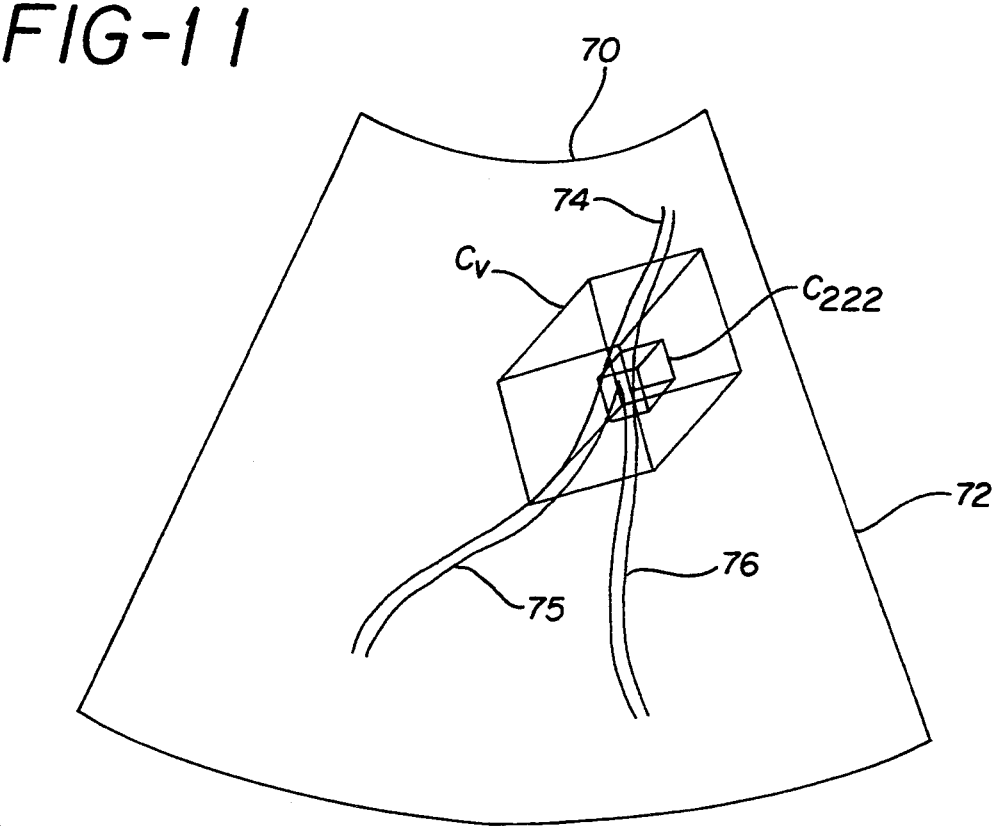
Figure 10:
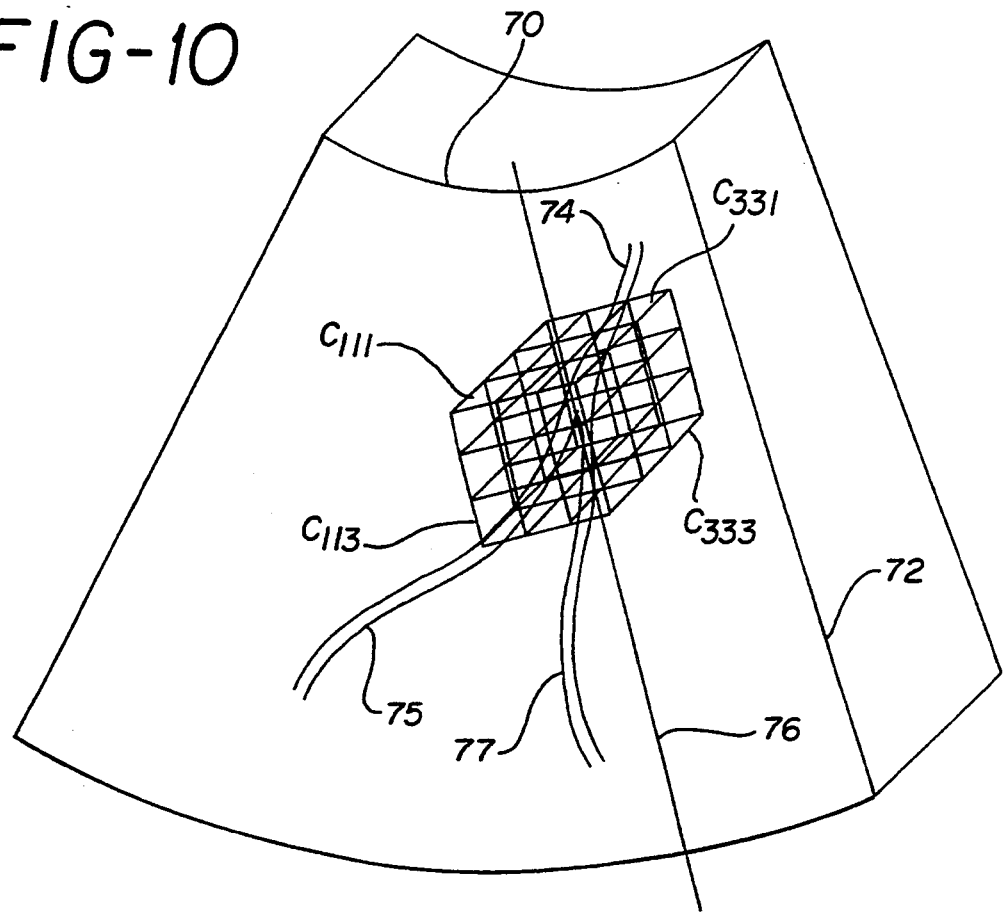
Figure 8:
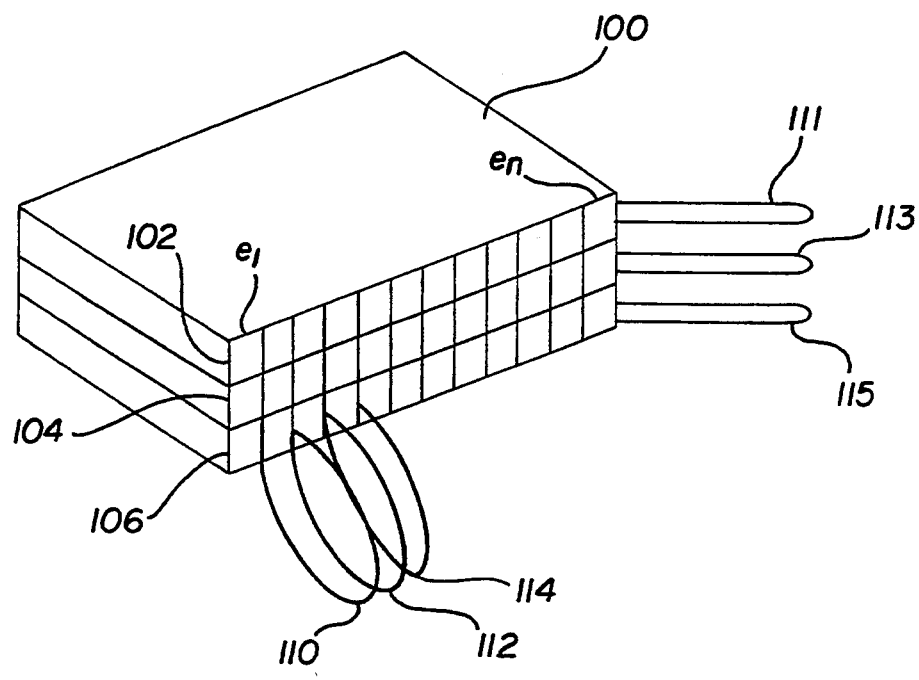

In the drawings:

FIGS. 1a, 1b, and 1c illustrate in block diagram form the portions of a Doppler measurement and display system constructed in accordance with the principles of the present invention;

FIGS. 2, 3, and 4 diagramatically illustrate Doppler measurement displays in accordance with the principles of the present invention;

FIGS. 5 and 6 illustrate M-mode and spectral Doppler displays produced in accordance with the principles of the present invention;

FIG. 7 diagramatically illustrates a Doppler measurement display in accordance with the principles of the present invention;

FIG. 8 schematically illustrates an elevational array transducer for use in accordance with the principles of the present invention;

FIG. 9 diagramatically illustrates a two dimensional Doppler measurement display in accordance with the principles of the present invention; and FIGS. 10 and 11 diagramatically illustrate three dimensional Doppler measurement displays in accordance with the principles of the present invention.

Referring first to FIGS. 1a and 1b, a Doppler measurement and display system constructed in accordance with the principles of the present invention is shown. A scanhead 10 transmits ultrasonic energy into the body of a patient being examined and receives echo information returned from inside the body. The ultrasonic energy may be directionally steered into the body by a mechanically translating transducer or by an electronically steered multielement array transducer 11. The received echo signals are coupled to a beamformer 12 which, as is well known in the art, subjects the echo signals from the individual elements of the transducer 11 to varying delays and combines them to form a properly consolidated and focused echo signal from a particular direction of return to the transducer. The direction of return is hereinafter referred to as the vector line of the ultrasonic echo signal.

The vector line echo signals are processed in two ways. A B mode detector 16 filters and detects the echo signals in the conventional manner for the production of a two dimensional B mode image of the internal structure of the body. The echo signals are also applied to a filter and demodulator 14 which processes the Doppler information of the echo signals to produce demodulated signals representative of frequency measurements or phase shifts of the echo signal along the vector line. In the preferred embodiment these demodulated Doppler signals are complex and in the form of digital I and Q values taken from discrete spatial locations along the vector line known as sample volumes or cells. The I and Q values from one cell location form a vector which contains the Doppler shift information. The Doppler shift (generally characterized as a phase or frequency shift) is proportional to the velocity of fluid flow at that cell location.

The Doppler signals are then accumulated in a plurality of parallel processing channels as a function of the cell location from which they were acquired. The Doppler signals from cell location $C_1$ are passed through a wall filter 20 to eliminate low velocity signals derived from moving tissue, such as vessel walls and valves, as opposed to the desired fluid flow velocity signals. The filtered velocity signals, indicated as C1 in FIG. 1a, are then applied to a power estimator 22 which develops an estimate of the average power of the Doppler signals from cell $C_1$. The power estimator performs a calculation of the form $$R_{c,t}[0] = \frac{1}{M} \sum_{m=t}^{t+M-1} x_c[m]x_c^*[m]$$

where $x_c[m]$ is the complex Doppler sample from location c at time index m, $x_c^*[m]$ is the complex conjugate of $x_c[m]$, and M is the number of complex Doppler samples acquired from location c from which the average power is estimated. The estimated power parameters $R_{c,t}[0]$ are filtered by a smoothing filter 24 to produce a Doppler signal power parameter $P_{(1)}$ for the first cell location.

Doppler signals from a plurality of other cell locations are processed in similar channels as shown in FIG. 1a. Shown in the drawing are a second channel which produces a second Doppler signal power parameter $P_{(2)}$ for a second cell location and the $n^{th}$ channel which produces a Doppler signal power parameter P(n) for the $n^{th}$ cell location.

The Doppler power estimates are applied to the inputs of a comparison and selection processor 50 which compares the magnitudes of the power estimates and selects the maximum value parameter. The selected maximum value is applied to the control input of a selection circuit 52 which selects the Doppler signals produced from the corresponding cell. The selected Doppler signals and their cell location indicator are applied to the input of a Doppler display processor 54, together with the B mode data from the B mode detector 16 and locational information from the beamformer 12. The Doppler signals are processed to produce a Doppler spectrum as is known in the art and the B mode data, locational data, and cell location indicator are used to produce a spatial display of the internal structure of the body and corresponding cell locations.

A typical spatial display produced in accordance with the principles of the present invention is shown in FIG. 2. This drawing shows the outline 72 of a sector field wherein the scanhead is positioned above the arcuate line 70. The B mode data is used to form a spatially oriented image of structure within the body such as the small blood vessel 74 with two branches 75 and 77. A Doppler vector line 76 is shown in the image along which are located a number of contiguous sample volumes or cells $C_1$, $C_2$, $C_3$, $C_4$, ... $C_n$. In the illustrated example the clinician is trying to measure the blood flow velocity at the point where the small vessel branches. To obtain precise, highly accurate information the size of the cell is made very small so that it will correspond in size to the small diameter of the vessel. With prior techniques a single sample volume cell would be used and the clinician would try to maintain the cell positioned within the vessel. Small movements of the scanhead or the body such as motion due to the respiration of the patient makes the acquisition of a continuous stream of Doppler data from the desired location extremely difficult. The present invention overcomes this difficulty by providing a plurality of sample volume cells which are continuously monitored and automatically changed to continuously track the location of the vessel.

For instance, in the drawing it is seen that cell $C_4$ is positioned over the vessel 74 and the other cells are located on either side of the vessel. The cell exhibiting the greatest intensity of returning Doppler signals, as indicated by the most significant measured Doppler power, would be cell $C_4$. The spectral Doppler display would under these conditions be that which is developed from the Doppler information of cell $C_4$ and selected by the power estimator. In FIG. 2 the selected cell $C_4$ is highlighted, colored, or otherwise visually distinguished in the display. A typical scrolling spectral Doppler display is shown at the bottom of FIG. 5 to the right of axis A1 during time period $t_1$ as indicated by curve 80. The curve 80 in FIG. 5 represents the peak magnitudes of the Doppler spectral lines and is produced as explained in U.S. patent application Ser. No. 892,301, entitled "Continuous Display of Peak and Mean Blood Flow Velocities" and filed Jun. 2, 1991, the contents of which are incorporated herein by reference.

Now assume that there is some motion of the body or the scanhead such that the vessel is no longer spatially aligned with cell $C_4$. The vessel may now be aligned with one of the other cells, such as cell C3 or cell C5, for instance. The newly aligned cell would now return the maximum Doppler power and the selectors 50 and 52 would now apply the Doppler signals of the newly aligned cell to the processor 54. The vessel 74 would now be seen in FIG. 2 to be spatially aligned with the different highlighted cell and the spectral display at the bottom of FIG. 5 would produce a new axis line A2 to indicate to the user that the cell location had shifted. The spectral display would now begin to produce a spectral display from the new cell location as indicated by curve 82 during the subsequent time period $t_2$. Thus it is seen that an embodiment of the present invention will constantly monitor multiple sample volumes and continuously track the sample volume location which is of interest to the clinician.

While the preferred embodiment is shown to track the vessel 74 on the basis of Doppler signal power estimation, it will be apparent that a subset of other measures of clinical interest, such as signal intensity, bandwidth, or frequency could also be used as the selection criterion.

The spectral display of the present invention can provide even greater clinical benefit when used with other ultrasonic diagnostic techniques. For instance, a time-motion or M-mode display is shown above the spectral display in FIG. 5. These M-mode curves show spatial variation of the interfaces of the body along the Doppler vector line 76 as a function of time. Each of the illustrated M-mode curves corresponds to one of the cell locations of FIG. 2. To indicate correspondence between the M-mode curves and the spectral information, the M-mode curve of the cell which is being spectrally display can be highlighted, colored, or otherwise distinguished in the display. As the multi sample volume Doppler system shifts to a different cell location the highlighted or colored M-mode curve would change correspondingly, thereby producing a continuous, reproducible record of M-mode and spectral information.

To eliminate undesired rapid shifting of the spectral line data during conditions of erratic patient or scanhead motion, a desired degree of hysteresis can be designed into the comparison and selection processor 50 or the selection circuit 52. This would prevent the selection circuit 52 from selecting the signals of a new cell until a different power estimation parameter is greater than the present one by a given amount or continues to exceed the present one for a given amount of time, for instance. An alternative technique for achieving substantially the same effect is shown in FIG. 4. This drawing is similar to that of FIG. 2 except that the cells $C_1$, $C_2$, $C_3$, ... $C_n$ are seen to overlap the adjacent cells. Thus, the power estimation of a given cell will also include some energy that is also present in the measurement of its adjacent neighbors. The overlap of spatial sample volume locations will thus provide a degree of smoothing in transitions from a given cell location to its adjacent neighbors.

Referring to FIG. 1c in conjunction with FIG. 1a, a technique for producing simultaneous spectral lines is shown. In FIG. 1c the Doppler information from each channel is separately processed in parallel in a number of spectral display processors 26, 36, ... 46. The spectral data is applied to a video processor 56 together with the respective power estimations $P_{(1)}$, $P_{(2)}$, ... $P_{(n)}$. The video processor 56 is then enabled to produce displays as shown in FIGS. 6 and 7. FIG. 6 shows a plurality of scrolling spectral curves 90, 92, 94, and 96, each being of the Doppler spectrum at a different cell location. The intensity or brightness of each curve on the display is modulated as a function of the Doppler power from the corresponding cell location.

If cell location $C_2$ is returning the greatest power and curve 92 corresponds to cell location $C_2$, then curve 92 would be more brightly displayed than the other curves, for instance. Such a display would find utility when studying the flow conditions of a large vessel such as vessel 78 in FIG. 7. The cells $C_1$, $C_2$, $C_3$, ... $C_n$ are seen to be spanning vessel 78 between the vessel walls 78a and 78b and the spectral curves of FIG. 6 indicate flow conditions at points across the vessel 78.

The preceding examples have illustrated multiple sample volume tracking along a one dimensional vector line. The principles of the present invention may also be applied to two and three dimensional embodiments. A scanning and processing technique known as multiline, shown for instance in U.S. Pat. No. 4,644,795, may be used to simultaneously acquire Doppler information in a plurality of directions. This technique allows acquisition, processing, and tracking of Doppler information simultaneously along a plurality of vector lines. FIG. 9 illustrates application of the technique to acquire Doppler information along the row of cells $C_{12}$ ... $C_{n2}$ of vector line 76, as well as two adjacent rows $C_{11}$ ... $C_{n1}$ and $C_{13}$ ... $C_{n3}$. The Doppler information from each cell is processed in a separate channel or if processing speeds permit by time multiplexing of channel processors. The power estimates from all channel locations are monitored and compared and the spectral data from the cell location with the greatest Doppler power is displayed. Concurrently, the selected cell is highlighted in the two dimensional cell matrix of FIG. 9. In the illustrated example cell $C_{42}$ at the vessel junction may be identified as the selected cell and highlighted. The two dimensional matrix of cells allows tracking of the selected cell in two dimensions, laterally and longitudinally, as compared with the earlier embodiments.

An alternate technique for displaying the two dimensional cell matrix of FIG. 9 is shown in FIG. 3. In this drawing the area of the body being interrogated, $C_A$, is outlined. Only the selected sample volume $C_{max}$ in the cell area $C_A$ is shown individually. The cell $C_{max}$ will move around within the cell area $C_A$ as the patient or scanhead move.

An alternate technique for acquiring multiline data is shown in FIG. 8, which illustrates a two dimensional array 100 of transducer elements. Three rows 102, 104, and 106 of transducer elements are shown, each row comprising individual elements $e_1$ ... $e_n$. Preferably the beam patterns of the array rows are narrow in the elevational dimension as indicated by beam patterns 111, 113, and 115 which are seen to be nonoverlapping. The beam patterns in the longitudinal direction may overlap as shown by beam patterns 110, 112, and 114 to provide an effect similarly to that of the previously mentioned hysteresis effect. The beamformer could be time multiplexed between the individual rows of elements or, alternatively, each row of transducer elements could be coupled to a separate beamformer for parallel beamforming operation.

The two dimensional transducer array and multiple beamformer configuration can advantageously be used to track cell locations in three dimensions as shown in FIGS. 10 and 11. FIG. 10 shows the vessel 74, 75, 77 with a three cell by three cell by three cell cube surrounding the junction of vessel branches 75 and 77. The left front corner cells $C_{111}$ and $C_{113}$ are identified in the drawing, as are the right rear corner cells $C_{331}$ and $C_{333}$. The vector line 76 passes through the center of the cube of cells and also through the vessel branch junction. If the highest intensity Doppler return were occurring at this junction, then the central cell ($C_{222}$) in the cube would be highlighted and its Doppler spectrum displayed. It is apparent that this embodiment extends the benefit of the two dimensional cell area to three dimensions. Motion of the vessel junction in any of three dimensions can be tracked by the cube of sample volumes.

The display could also be shown in the simplified form of FIG. 11. In this drawing only the outline $C_V$ of the full cube of cells is shown on the display, together with the particular sample volume $C_{222}$ which is returning the Doppler signals of greatest intensity. The individual cell will move within the cube outline as different cells within the cube are selected for spectral display.

What is claimed is:

1. An ultrasonic diagnostic system for displaying Doppler information indicative of fluid flow within the body of a patient comprising:

means for transmitting ultrasonic energy into the body and receiving ultrasonic echo information from a plurality of sample volumes within the body;

means for processing said received ultrasonic echo information to obtain Doppler information associated with respective ones of said plurality of sample volumes;

means for comparing said Doppler information of said sample volumes to identify a sample volume most closely associated with Doppler information of a desired characteristic; and means, responsive to identification of a sample volume by said comparing means, for uniquely displaying a Doppler information attribute of said identified sample volume, wherein said comparing means monitors the Doppler information of said sample volumes while Doppler information of said identified sample volume is displayed to monitor the continued association of said sample volumes with said Doppler information of a desired characteristic.

2. The ultrasonic diagnostic system of claim 1, wherein said respective ones of said sample volumes are spatially contiguous within the body.

3. The ultrasonic diagnostic system of claim 1, further comprising means for evaluating the intensity of the Doppler signals associated with each of said respective ones of said sample volumes, and wherein said desired characteristic comprises Doppler signal intensity.

4. The ultrasonic diagnostic system of claim 1, further comprising means for evaluating the power of the Doppler signals associated with each of said respective ones of said sample volumes, and wherein said desired characteristic comprises maximum Doppler signal power.

5. The ultrasonic diagnostic system of claim 1, further comprising means for evaluating the frequency shift of the Doppler signals associated with each of said respective ones of said sample volumes, and wherein said desired characteristic comprises maximum Doppler frequency shift.

6. The ultrasonic diagnostic system of claim 1, further comprising: means for processing said received ultrasonic echo information to produce a B mode image; means responsive to said transmitting and receiving means for displaying sample volume locations within said image; and wherein said means for uniquely displaying comprises means responsive to said comparing means for displaying said identified sample volume within said image in a manner which distinguishes said identified sample volume within said image.

7. The ultrasonic diagnostic system of claim 6, wherein said means for displaying a Doppler information attribute of said identified sample volume comprises a spectral Doppler display.

8. The ultrasonic diagnostic system of claim 1, wherein each of said respective ones of said sample volumes is spatially contiguous with another sample volume.

9. The ultrasonic diagnostic system of claim 1, wherein each of said respective ones of said sample volumes spatially overlaps another sample volume.

10. The ultrasonic diagnostic system of claim 1, wherein said means for transmitting ultrasonic energy into the body and receiving ultrasonic echo information from a plurality of sample volumes within the body comprises means for receiving ultrasonic echo information from a plurality of sample volumes located along each of a plurality of vector lines emanating from said transmitting means, and wherein said respective ones of said sample volumes are spatially located on a plurality of said vector lines.

11. The ultrasonic diagnostic system of claim 10, wherein said respective ones of said sample volumes are spatially located over a two dimensional area.

12. The ultrasonic diagnostic system of claim 11, wherein said means for uniquely displaying a Doppler information attribute of said identified sample volume further comprises means for identifying said two dimensional area and means for identifying said identified sample volume within said area.

13. The ultrasonic diagnostic system of claim 1, wherein said means for uniquely displaying a Doppler information attribute of said identified sample volume comprises means for concurrently displaying Doppler information attributes of a plurality of said sample volumes and means for uniquely designating the displayed Doppler information attribute associated with said identified sample volume.

14. An ultrasonic diagnostic system for displaying Doppler information indicative of fluid flow within the body of a patient comprising:

means for transmitting ultrasonic energy into the body and receiving ultrasonic echo information from a plurality of sample volumes within the body;

means for processing said received ultrasonic echo information to obtain Doppler information associated with respective ones of said plurality of sample volumes;

means for monitoring said Doppler information of respective ones of said sample volumes to identify a first sample volume that best satisfies a criterion of said Doppler information;

means, responsive to said monitoring means, for displaying Doppler information of said identified sample volume, and for displaying Doppler information of a second sample volume when said monitoring means identifies the Doppler information of said second sample volume as best satisfying said criterion; and means, associated with said display of Doppler information, for displaying a change of said displayed Doppler information in correspondence with a change of said identified sample volume.

15. The ultrasonic diagnostic system of claim 14, wherein said means for displaying the Doppler information of said identified sample volume comprises a spectral Doppler display, and wherein said means for displaying a change of said Doppler information comprises means for successively displaying a different spectral Doppler signal in correspondence with a change of the identified sample volume.

16. The ultrasonic diagnostic system of claim 15, wherein said means for displaying Doppler information of said identified sample volume comprises means for concurrently displaying the Doppler information associated with a plurality of said sample volumes and wherein said means for displaying a change of said Doppler information comprises means for highlighting a different one of said concurrent displays of Doppler information.

17. An ultrasonic diagnostic system for displaying Doppler information indicative of fluid flow within the body of a patient comprising:

means for transmitting ultrasonic energy into the body and receiving ultrasonic echo information from a plurality of sample volumes spatially located within a three dimensional volume within the body;

means for processing said received ultrasonic echo information to obtain Doppler information associated with respective ones of said plurality of sample volumes;

means for continuously comparing said Doppler information of respective ones of said sample volumes to identify a sample volume most closely associated with Doppler information of a desired characteristic; and means for uniquely displaying information concerning the sample volume which is the current identified sample volume while said Doppler information is being compared.

18. The ultrasonic diagnostic system of claim 17, further comprising means responsive to said transmitting and receiving means for producing a spatial display of said three dimensional volume; and means, responsive to said comparing means, for indicating the location of said identified sample volume in said spatial display.

19. An ultrasonic diagnostic system for displaying Doppler information indicative of fluid flow within the body of a patient comprising:

means for transmitting ultrasonic energy into the body and receiving ultrasonic echo information from a plurality of sample volumes within the body, which sample volumes are spatially located along a vector line;

means for processing said received ultrasonic echo information to obtain Doppler information associated with respective ones of said plurality of sample volumes;

means for comparing said Doppler information of respective ones of said sample volumes to identify a sample volume associated with Doppler information of a desired characteristic;

means, responsive to said received ultrasonic echo information, for displaying variations of said echo information along said vector line as a function of time; and means, responsive to said comparing means, for displaying the Doppler information of said identified sample volume.

20. The ultrasonic diagnostic system of claim 19, wherein said means for displaying variations of said echo information along said vector line further comprises means for indicating the spatial location of said identified sample volume.

* * * * *